(12) United States Patent
Cherif

(10) Patent No.: US 6,905,828 B2
(45) Date of Patent: Jun. 14, 2005

(54) FLUORESCENT PROBES FOR CHROMOSOME PAINTING

(75) Inventor: Dorra Cherif, Paris (FR)

(73) Assignee: Genset S.A. (FR)

(*) Notice: Subject to any disclaimer, the term of this patent is extended or adjusted under 35 U.S.C. 154(b) by 0 days.

(21) Appl. No.: 10/251,699

(22) Filed: Sep. 19, 2002

(65) Prior Publication Data

US 2003/0099989 A1 May 29, 2003

Related U.S. Application Data

(62) Division of application No. 09/418,804, filed on Oct. 15, 1999, now Pat. No. 6,562,959.

(30) Foreign Application Priority Data

Oct. 15, 1998 (FR) .............................. 98 12957

(51) Int. Cl.$^7$ .......................... C12Q 1/68; C12P 19/34; C07H 21/02; C07H 21/04; C07H 21/00
(52) U.S. Cl. ........................ 435/6; 435/91.1; 435/91.2; 435/91.51; 536/23.1; 536/24.3; 536/24.33; 536/25.3; 536/25.32
(58) Field of Search .................... 435/6, 91.1, 91.2, 435/183, 91.51; 436/94; 536/23.1, 24.3, 24.31, 24.33, 25.3, 25.32

(56) References Cited

U.S. PATENT DOCUMENTS 5,817,462 A  10/1998 Garini et al.

FOREIGN PATENT DOCUMENTS

WO  WO 98/38333  9/1998

OTHER PUBLICATIONS

Wilgenbus et al., IRS–long range (LR) PCR: a simple method for efficient amplification of human genomic DNA from complex sources. Methods in Molecular and Cellular Biology, 5, 214–221, 1995.*
Muller et al., Comparative fluorescence in situ hybridization mapping of primate chromosomes with Alu polymerase chain reaction generated probes from human.rodent somatic cell hybrids. Chromosome Research, 4, 38–42, 1996.*
Cherif, et al., Proc. Natl. Acad. Sci. USA, vol. 87, pp. 6839–6843, Sep. 1990 "Simultaneous localization of cosmids and chromosome R–banding by fluorescence microscopy: Application to regional mapping of human chromosome 11".
Korenberg, et al., Cell, vol. 53, pp. 391–400, May 8, 1988 "Human Genome Organization: Alu, Lines, and the Molecular Structure of Metaphase Chromosome Bands".
Ledbetter, et al., Genomics, vol. 8, pp. 614–622, 1990 "PCR–Karyotype' of Human Chromosomes in Somatic Cell Hybrids".

Ledbetter, et al., Genomics, vol. 6, pp. 475–481, 1990 "Rapid Isolation of DNA Probes within Specific Chromosome Regions by Interspersed Repetitive Sequence Polymerase Chain Reaction".
Lengauer, et al., Hum Genet, vol. 86, pp. 1–6, 1990 "Painting of human chromosomes with probes generated from hybrid cell lines by PCR with Alu and L1 primers".
Lichter, et al., Proc. Natl. Acad. Sci. USA, vol. 87, pp. 6634–6638, Sep. 1990 "Fluorescence in situ hybridization with Alu and L1 polymerase chain reaction probes for rapid characterization of human chromosomes in hybrid cell lines".
Pinkel, et al, Proc. Natl. Acad. Sci. USA, vol. 83, pp. 2934–2938, May 1986 "Cytogenetic analysis using quantitative, high–sensitivity, fluoresence hybridization".
Romana, et al., Eur J Hum Genet, vol. 1, pp. 245–251, 1993 "A Simple Method for Prenatal Diagnosis of Trisomy 21 on Uncultured Amniocytes".
Sabile, et al., Mammalian Genome, vol. 8, pp. 81–85, 1997 "Isolation of monochromosomal hybrids for mouse Chromosomes 3, 6, 10, 12, 14, and 18".
Schröck, et al., Science, vol. 273, pp. 494–497, Jul. 26, 1996 "Multicolor Special Karyotyping of Human Chromosomes".
Speicher, et al., Nature Genetics, vol. 12, pp. 368–375, Apr. 1996 "Karyotyping human chromosomes by combinatorial multi–fluor FISH".
Wilgenbus, et al., Methods in Molecular And Cellular Biology, vol. 5, pp. 214–221, 1995 "IRS–Long Range (LR) PCR: A Simple Method for Efficient Amplification of Human Genomic DNA From Complex Sources".
Darnell, J., et al., "Molecular Cell Biology"; $2^{nd}$ edition., Scientific American Books, Chapter 10, "Eukaryotic Chromosomes and Genes Molecular Anatomy", pp. 370–371.
Dutrillaux, B., et al., "Cytogenetique Humaine—Sur une nouvelle technique d'analyse du caryo–type humain", C.R.Aca.Sc. Paris, t. 272 (17 mai 1971): pp. 2638–2640— Serie D.

(Continued)

Primary Examiner—Kenneth R. Horlick
Assistant Examiner—Frank W Lu
(74) Attorney, Agent, or Firm—Saliwanchik, Lloyd & Saliwanchik

(57) ABSTRACT

The present invention relates to fluorescent probes which can be used in multicolor fluorescence in situ hybridization, and mainly chromosome painting. The probes intended for labeling a chromosome are such that they are composed of a set of DNA segments which are more represented in certain chromosome bands and which are obtained by IRS-PCR amplification from said chromosomes using PCR primers specific for the repeated and dispersed Alu and LINE DNA sequences.

The invention comprises, in addition, methods of producing said probes, multicolor FISH methods which can use said probes as well as diagnostic kits comprising them.

Finally, the invention comprises combinations of fluorophores and optical filters.

9 Claims, No Drawings

OTHER PUBLICATIONS

Henegariu, O., et al., "Colour–changing karyotyping: an alternative to M–FISH/SKY", *Nature Genetics* (1999), 23:263–4.

Johnson, G.D., et al., "A Simple Method of Reducing the Fading of Immunofluorescence During Microscopy", *J. Immunol. Meth.* (1981), 43:349–350; Elsevier/North–Holland Biomedical Press.

Sabile, A., et al., "Isolation of monochromosomal hybrids for mouse Chromosomes 3, 6, 10, 12, 14, and 18", *Mammalian Genome* (1997), 8:81–85; Springer Verlag New York, Inc.

Sumner, A.T., et al., "New Technique for Distinguishing between Human Chromosomes", *Nature New Biology* (1971), 232:31–32.

www.probes.com/handbook; Molecular Probes; 1996, Molecular Probes, Inc.

* cited by examiner

FLUORESCENT PROBES FOR CHROMOSOME PAINTING

CROSS-REFERENCE TO RELATED APPLICATIONS

The present invention is a divisional of U.S. application Ser. No. 09/418,804, filed Oct. 15, 1999, now U.S. Pat. No. 6,562,959, which claims priority to French Application No. FR 98/12957, filed Oct. 15, 1998, pending, each of which is hereby incorporated by reference herein in its entirety, including any figures, tables, nucleic acid sequences, amino acid sequences, or drawings.

The present invention relates to chromosome painting and more particularly the fluorescent probes which can be used in methods such as the FISH ("Fluorescence In Situ Hybridization") method. The invention also relates to combinations of fluorophores and of optical filters.

In situ hybridization is a technique which makes it possible to detect a DNA (or RNA) sequence by means of a probe having a specific sequence which is homologous to that studied. It is based on the complementarity of the nucleotides (A/T, A/U, G/C) and it can be carried out under precise physicochemical conditions on chromosome or tissue preparations. The result of the in situ hybridization process is the formation of a hybrid between a probe and a target. In situ hybridization includes a denaturing step and also a step for detecting the hybrid or the probe which is carried out after the in situ hybridization of the probe to the target. The sample may adhere in the form of a layer to the surface of the slide and this sample may, for example, comprise or contain individual chromosomes or chromosomal regions which have been treated in order to maintain their morphologies under denaturing conditions. In the context of fluorescence in situ hybridization, the probes are labeled with a fluorophore and the hybridization is revealed by fluorescent labeling.

The recent development of this technique allows the simultaneous visualization, on the same preparation, of several probes each revealed by a different fluorophore. This technique, called multicolor FISH or multi-FISH, has been made possible by the combination of filters specific for the wavelengths of emission of the different fluorescent molecules ensuring the labeling with the aid of a computer-aided imaging carried out by means of infrared-sensitive high-resolution cold CCD cameras (Schröck et al., 1996; Speicher et al., 1996).

The use of probes having a specific sequence homologous to a precise chromosomal sequence or a whole chromosome coupled with the potential for a multicolor fluorescent labeling makes it possible to develop so-called chromosome painting techniques, that is to say to obtain chromosomes of different colors and thus to obtain, if desired, a multicolor complete karyotype. Karyotype is understood to mean the characteristic arrangement of the chromosomes of a cell in the metaphase.

Within the general meaning of the term, "labeling" is understood to mean an entity such as a radioactive isotope or a nonisotopic entity such as enzymes, biotin, avidin, steptavidin, digoxygenin, luminescent agents, dyes, haptens and the like. The luminescent agents, depending on the source of excitation energy, may be classified into radioluminescent, chemoluminescent, bioluminescent and photoluminescent (including fluorescent and phosphorescent) agents. The term "fluorescent" refers in general to the property of a substance (such as a fluorophore) to produce light when it is excited by an energy source such as ultraviolet light for example.

"Chromosomal paint probe" is understood to mean a probe or a probe composition such as the probe composition of this invention, which is suitable for hybridizing, under hybridization conditions, with a target which comprises a predetermined chromosome of a multichromosomal genome. If only a fraction of such a chromosome is present in the sample being subjected to such a hybridization with such a probe composition, then this fraction hybridizes and is identified. In practice, a painted probe of this invention may be mixed with a second, a third, and the like, so as to allow the labeling and the simultaneous detection of the two, three, and the like, predetermined chromosomes.

The visualization of all the 24 human chromosomes has been made possible by the use of a labeling with a combination of fluorochromes. For example, in the case of the use of 5 different fluorophores, 31 combinations of fluorophores can be obtained. By using this labeling principle and 24 DNA probes specific for each of the human chromosomes, it has been possible to visualize each chromosome differentially. The attribution, by computer processing, of artificial colors to each of the combinations of fluorophores thus makes it possible to color the 24 human chromosomes differently.

Rapidly, the strong potentials of such a multicolor labeling have allowed the analysis of chromosomal aberrations which were difficult to detect up until now by conventional cytogenetic techniques for labeling chromosomes in bands (Summer et al., 1971; Dutrillaux and Lejeune, 1971) (Giema staining, labeling with BrdU, and the like). The principle of labeling of chromosomes in bands is based on the differences in the average base pair composition (richness in GC) between the bands and on the differences in the compaction of the chromatin between the chromosome bands. Chromosome painting has proved to be a very useful tool for detecting interchromosomal aberrations such as translocations, amplified DNA sequences such as the homogeneously stained regions called HSR (HSR for Homogeneously Staining Regions) or the excesses of chromosomal materials such as the marker chromosomes or double-minute chromosomes. Intrachromosomal aberrations such as deletions and duplications will only be detected as a function of the size of the aberrations, if the latter affect the length of the chromosomes, whereas chromosomal inversions will not at all be detectable by this method.

The limits of the use of the current spectral karyotyping as such are due to the fact that it does not make it possible to detect the nature of the chromosome bands involved in an inter- or intrachromosomal rearrangement. To do this, it is essential to couple this technique to the more conventional one of chromosome bands (R or G labeling) such as DAPI counterstaining, Giemsa or propidium iodide staining for example.

The requirement to combine different techniques of course constitutes a handicap in the analysis of chromosomal aberrations and, moreover, the use of the FISH or multi-FISH method which combines the high cost of the apparatus and the instrumentation necessary for the visualization of chromosome painting with the high cost of the probes specific for the chromosomes restricts the possibilities of this technique spreading to research laboratories or to diagnostic laboratories.

Paint probes currently available on the market (GIBCO-BRL, Oncor, Boehringer Manheim and the like) are obtained by DOP-PCR amplification using degenerate PCR primers of chromosomes or for fragments of chromosomes isolated by cumbersome techniques such as chromosome sorting by flow cytometry or microdissection of chromosomes. The hybridization of probes obtained by DOP-PCR does not generate chromosome bands on the chromosomes. The generation of chromosome bands was sought through the creation of artificial bands along chromosomes. This creation of artificial bands requires the use of cumbersome and expensive techniques. Furthermore, it results in bands which are not known reference marks in the field of cytogenetics.

Some others have described the use of chromosome paint probes obtained by amplification of chromosomes by IRS-PCR (Interspersed Repeated Sequences) using primers specific for DNA sequences which are repeated and dispersed in the genome, such as the Alu and LINE sequences. The combined use of LINE and Alu PCR primers for the amplification of human chromosomes by ISR-PCR was previously proposed by Lichter et al., 1990. However, the labeling in R bands which was obtained by the latter does not make it possible to ensure complete painting covering all the regions of the genome, in particular the telomeric regions and certain G chromosome bands.

The object of the present invention is to provide chromosomal probes which can be obtained inexpensively and which, in addition, make it possible to cause quality chromosome bands to appear directly on chromosomes painted in their entirety.

To do this, the present invention relates to probes intended for the labeling of a chromosome, characterized in that they are composed of a set of DNA segments which are more represented in certain chromosome bands and which are obtained by IRS-PCR amplification from said chromosomes with the aid of primers specific for the Alu and LINE DNA sequences.

The term "probe" refers to a polynucleotide or a mixture of polynucleotides such that DNA segments or DNA sequences are chemically combined with labeled individual entities. Each of the polynucleotides constituting a probe is characteristically in single-stranded form at the time of hybridization to the target.

The term "DNA fragment", "DNA segment" generally indicates only a portion of the polynucleotide or of a sequence present in a chromosome or a chromosome portion. A polynucleotide for example may be cut or fragmented into a multitude of segments or of fragments. A chromosome characteristically contains regions which have DNA sequences containing repeated DNA segments. The term "repeated" refers to the fact that a particular DNA segment is present many times (at least twice), dispersed or otherwise in the genome. The so-called IRS-PCR method using primers which hybridize with the dispersed repeated sequences of the genome, such as, for example, the Alu or LINE sequences.

"Genome" designates the complete and unique copy of the genetic instructions of an organism encoded by the DNA of this organism. In the present invention, the particular genome considered is multichromosomal such that the DNA is distributed in the cell between several individual chromosomes. The human genome is composed of 23 pairs of chromosomes, of which an XX or XY pair determine the sex.

The term "chromosome" refers to the support for the genes carrying heredity in a living cell which is derived from chromatin and which comprises DNA and protein components (essentially histones). The conventional international system for identifying and numbering the chromosomes of the human genome is used here. The size of an individual chromosome may vary within a multichromosomal genome and from one genome to another. In the present case of the human genome, the total length of DNA of a given chromosome is generally greater than 50 million bp. By way of comparison, the total length of the human genome is $3 \times 10^9$ bp.

The genome of mammals contains repeated DNA sequences dispersed over the whole genome. In humans, the majority of this type of sequences is represented by the different families of Alu sequences, which are about $10^6$ in number and have in common a consensus sequence of 300 bp. The repeated LINES (or L1) sequences are, like the Alu sequences, widely distributed over the whole genome. They are nevertheless less numerous (about $10^4$). Their consensus sequence is about 6 kb. They are preferably situated in the dark G bands (positive G or negative R), whereas the Alu sequences are instead situated in the dark R bands (positive R) (Korenberg and Kirowski, 1988).

The DNA segments amplified by IRS-PCR according to the invention may have as source somatic hybrids, preferably rodent-human somatic hybrids, chromosomes or fragments of chromosome. The chromosomes or fragments of chromosome may be obtained by chromosome sorting by flow cytometry or by chromosome microdissection. Within the framework of the preferred embodiment of the present invention, the DNA segments amplified by IRS-PCR have as source mono-chromosomal rodent-human somatic hybrids.

The DNA segments amplified by IRS-PCR according to the invention are more represented in one type of cytogenetic band. The preferred cytogenetic bands are the G bands or the R bands. In the preferred embodiment of the present invention, the DNA segments amplified by IRS-PCR are more represented in R bands.

Repeated sequences, analogous to the human repeated sequences, are also found in the genome of rodents. However, the divergence of this type of sequences between humans and rodents is sufficiently important for there to be little homology between them. This divergence allows a selective amplification of DNA segments contained in the human chromosome when human-rodent hybrids are used. Thus, starting with the DNA of a human-rodent somatic hybrid and using primers specific for the Alu and/or L1 consensus sequence, it is possible to selectively amplify by PCR the DNA sequences between two repeated sequences ("inverted" position) separated by a distance <5 kb. The product of amplification thus obtained consists of a set of fragments (whose size varies approximately from 100 bp to 5 kb) which is representative of practically the entire human chromosome contained in the DNA of the somatic hybrid.

In general, the present invention is of course more particularly intended for producing probes specific for human chromosomes, although it is possible to envisage chromosome paintings for other cell types (Sabile et al., 1997).

The probes of the present invention are characterized in that the probes are derived from a mixture of two IRS-PCR amplification products which is composed of:
  PCR amplification product obtained using the primer specific for the Alu DNA sequences,
  PCR amplification product obtained using the primer specific for the Alu DNA sequences and the primer specific for the LINE DNA sequences.

The present invention relates to a method of producing probes intended for labeling human chromosomes, characterized in that said method comprises the mixing of two amplification products obtained by two IRS-PCR amplifications from said chromosomes using, on the one hand, PCR primers specific for the Alu and LINE DNA sequences, and, on the other hand, PCR primers specific for the Alu DNA sequences.

Any primer specific for the Alu or LINE sequences may be used in the present invention. Preferably, the primers specific for the Alu DNA sequences consist of the SR1 primer whose sequence is described in SEQ ID No 1 and the primer specific for the LINE DNA sequence is preferably the L1H primer whose sequence is described in SEQ ID Nos 2 and 3.

Alternatively, probes according to the present invention may also be derived from a mixture of two IRS-PCR amplification products which is composed of:
- PCR amplification product obtained using the primer specific for the LINE DNA sequences,
- PCR amplification product obtained using the primer specific for the Alu DNA sequences and the primer specific for the LINE DNA sequences.

The present invention also relates to a method of producing probes intended for labeling human chromosomes, characterized in that said method comprises the mixing of two amplification products obtained by two IRS-PCR amplifications from said chromosomes using on the one hand PCR primers specific for the Alu and LINE DNA sequences, and, on the other hand, PCR primers specific for the LINE DNA sequences.

The present invention also comprises the use of fluorophores and of filters whose combination makes it possible to ensure a chromosome painting providing very readable karyotypes, that is to say to obtain contrasted and well-defined chromosome paint colors.

Thus, the DNA probes described above are labeled directly or indirectly by fluorescence techniques. Non-exhaustively, the fluorophores used for the labeling may be chosen from markers of the cyanine, rhodamine, fluorescein, Bobipy, Texas Red, Oregon Green, Cascade Blue type. In particular, all the fluorophores cited in "Handbook of fluorescent probes and research chemicals" (Richard P Haugland, 1996, Molecular Probes, MTZ Spence Ed., more particularly p 145–146, 153, 155–156, 157–158, 161) can be used to label the probes of the present invention.

Preferably, the probes according to the invention are labeled with at least 1, 2, 3, 4 or 5 fluorophores chosen from the following group: fluorescein isothiocyanate (FITC), Texas Red (TR for Texas Red), cyanine 3 (Cy3), cyanine 5 (Cy5), cyanine 5.5 (Cy5.5), cyanine 7 (Cy7), Bodipy 630/650.

The preferred method for labeling the DNA probes is "Nick translation". However, the labeling may also be carried out by all the standard reactions for synthesis of DNA catalyzed by a polymerase and for labeling oligonucleotides. For example, the labeling may be carried out by the techniques of random priming, amplification or primer extension in situ.

The term "directly labeled probe" designates or describes a nucleic acid probe whose labeling after the formation of hybrid with the target is detectable without subsequent reagent treatment of the hybrid. The probes using the FITC, Texas Red, Cy3 and Cy5 fluorophores according to the present invention are directly labeled.

The term "indirectly labeled probe" designates or describes a nucleic acid probe whose labeling after the formation of hybrid with the target must undergo an additional reagent treatment with one or more reagents in order to combine therewith one or more entities from which a detectable compound finally result(s). For example, the probes may be labeled with DNP, digoxigenin or biotin and the revealing comprises bringing the probe into contact with an anti-DNP or anti-digoxigenin antibody labeled with a fluorophore or with an avidin coupled to a fluorophore. The probes using the fluorophores Cy7, Bodipy 630/650, Cy5.5. according to the present invention are indirectly labeled.

Preferably, the probe composition of the present invention comprises the largest possible number of "directly labeled" probes. In addition to the fact that the directly labeled probes are easier to use, they allow better resolution. This good resolution is important for good observation of the chromosome bands. Preferably, the probe composition of the present invention is of the "direct labeling" type for all the fluorophores. A preferred probe composition of the present invention is of the "direct labeling" type for 4 of the 5 fluorophores used. In another preferred composition, the directly labeled probes represent 3 probes out of 5 or 6 fluorophores used.

The present invention also relates to a set of probes intended for labeling human chromosomes, characterized in that it contains probes according to the present invention for each of the human chromosomes and for a number of them. This set of probes will make it possible to analyze in a single operation a complete karyotype so as to detect therein and to identify therein possible chromosomal aberrations as described above.

The present invention also relates to a multicolor FISH method intended for studying the karyotype, characterized in that the DNA probes are labeled with fluorophores and in that each fluorophore having a specific absorption and emission wavelength is combined with a pair of optical filteres, one for absorption and one for emission.

The fluorophores are chosen such that the overlapping of the absorption and emission spectra between the different fluorophores is minimal. More particularly, it is important that there is no overlapping between the absorption and emission maxima of the different fluorophores.

Each fluorophore is used with a pair of optical filters; one for absorption and one for emission. The filters make it possible to select the passbands such that the wavelengths corresponding to an overlap with another fluorophore are eliminated. Accordingly, the filters used in the present invention are preferably of the narrow passband optical filter type. The filters are preferably of a superior quality because it is important that the filter does not allow light outside the passband to pass through.

Preferably, the present invention also relates to a multi-color FISH method intended in particular for studying the karyotype, characterized in that the DNA probes according to the present invention are labeled with fluorophores and in that each fluorophore having a specific absorption and emission wavelength is combined with a pair of optical filters, one for absorption and the other for emission, said method using fluorophores and pairs of filters chosen from the following group:
  a) the fluorophore FITC having a maximum absorption wavelength of 494 nm and a maximum emission wavelength of 517 nm combined with an excitation filter of the 490DF30 type (Omega Optical) and with an emission filter of the 530DF30 type (Omega Optical),
  b) the fluorophore Cy3 having a maximum absorption wavelength of 554 nm and a maximum emission wavelength of 568 nm combined with an excitation filter of the 546DF10 type (Omega Optical) and with an emission filter of the 570DF10 type (Omega Optical),
  c) the fluorophore TR having a maximum absorption wavelength of 593 nm and a maximum emission wavelength of 613 nm combined with an excitation filter of the 590DF10 type (Omega Optical) and with an emission filter of the 615DF10 type (Omega Optical),
  d) the fluorophore Cy5 having a maximum absorption wavelength of 652 nm and a maximum emission wavelength of 670 nm combined with an excitation filter of the 650DF20 type (Omega Optical) and with an emission filter of the 670DF10 type (Omega Optical), e) the fluorophore Cy7 having a maximum absorption wavelength of 743 nm and a maximum emission wavelength of 767 nm combined with an excitation filter of the 740DF25 type (Omega Optical) and with an emission filter of the 780EFLP type (Omega Optical), f) the fluorophore Cy5.5 having a maximum absorption wavelength of 675 nm and a maximum emission wavelength of 694 nm combined with an excitation filter of the 680DF20 type (Omega Optical) and with an emission filter of the 700EFLP type (Omega Optical), g) the fluorophore Bodipy 630/650 having a maximum absorption wavelength of 632 nm and a maximum emission wavelength of 658 nm combined with an excitation filter of the 630DF20 type (Omega Optical) and with an emission filter of the 650DF10 type (Omega Optical).

The invention also relates to a multicolor FISH diagnostic kit characterized in that it comprises DNA probes according to the present invention labeled with fluorophores and in that each fluorophore having a specific absorption and emission wavelength is combined with a pair of optical filters, one for absorption and one for emission, said kit using fluorophores and pairs of filters chosen from the following group:

a) the fluorophore FITC having a maximum absorption wavelength of 494 nm and a maximum emission wavelength of 517 nm combined with an excitation filter of the 490DF30 type (Omega Optical) and with an emission filter of the 530DF30 type (Omega Optical), b) the fluorophore Cy3 having a maximum absorption wavelength of 554 nm and a maximum emission wavelength of 568 nm combined with an excitation filter of the 546DF10 type (Omega Optical) and with an emission filter of the 570DF10 type (Omega Optical), c) the fluorophore TR having a maximum absorption wavelength of 593 nm and a maximum emission wavelength of 613 nm combined with an excitation filter of the 590DF10 type (Omega Optical) and with an emission filter of the 615DF10 type (Omega Optical), d) the fluorophore Cy5 having a maximum absorption wavelength of 652 nm and a maximum emission wavelength of 670 nm combined with an excitation filter of the 650DF20 type (Omega Optical) and with an emission filter of the 670DF10 type (Omega Optical), e) the fluorophore Cy7 having a maximum absorption wavelength of 743 nm and a maximum emission wavelength of 767 nm combined with an excitation filter of the 740DF25 type (Omega Optical) and with an emission filter of the 780EFLP type (Omega Optical), f) the fluorophore Cy5.5 having a maximum absorption wavelength of 675 nm and a maximum emission wavelength of 694 nm combined with an excitation filter of the 680DF20 type (Omega Optical) and with an emission filter of the 700EFLP type (Omega Optical), g) the fluorophore Bodipy 630/650 having a maximum absorption wavelength of 632 nm and a maximum emission wavelength of 658 nm combined with an excitation filter of the 630DF20 type (Omega Optical) and with an emission filter of the 650DF10 type (Omega Optical).

The filters according to the present invention are preferably such that:
they are of the 6-cavity type,
they have an ADI of 0°;
they have a tolerance $\lambda_0 \pm 20\%$ of FWHM,
they have a tolerance on FWHM of $\pm 20\%$ of FWHM,
they have an OD5 out-of-passband rejection for UV at 1200 nm
they have a transmission curve $T \geq 50\%$ at $\lambda_0$.

Preferably, the filters must also have a centered useful diameter greater than 21 mm, and a thickness $\leq 7$ mm, The fluorophores and the above filters may be used for the labeling of the probes according to the present invention or alternatively for different probes used, for example, for chromosome painting or for multicolor FISH.

In the present invention, "filters" is understood to mean narrow passband interference filters which transmit light within a given very narrow spectral band centered around the reference wavelength $\lambda_0$. They are characterized by their transmission curve: $T=f(\lambda)$. The width of the band is defined by the full width at half maximum transmission (FWHM for "Full Width at Half Maximum transmission").

Outside the passband, the filter allows a residual signal which is as attenuated as possible to pass through.

The interference filters function on the principle of constructive and destructive interference. The basic component of an interference filter is called cavity. It has two stacks of reflectors separated by a layer of a dielectric solid. The higher the number of cavities, the more rectangular the shape of the transmission curve (that is to say the greater the slope of this curve). Moreover, the higher the number of cavities, the better the coefficient of attenuation outside the passband.

For the multifluorescence application, the excitation or emission spectra of the fluorochromes used are very close to each other. It is therefore necessary to recover the minimum amount of signal possible outside the passband. Accordingly, 6-cavity filters which offer the best characteristics at this level were chosen.

The filters used preferably have the following specifications:
they are designed to be used at normal light incidence,
the tolerance on the centre wavelength ($\lambda_0$) is $\pm 20\%$ of the passband, for example, for a filter with a passband of 10 nm, $\lambda_0$ will be defined with a tolerance of $\pm 2$ nm,
the tolerance on the width of the passband is $\pm 20\%$,
the coefficient of transmission T of these filters is greater than 50%,
the out-of-passband rejection of these filters is 5OD for ultraviolet at 1200 nm; this means that outside the passband, the coefficient of transmission is $10^{-5}$, that is to say 0.001%. For standard filters, the out-of-passband rejection is ensured for wavelengths ranging from 0.8 $\lambda_0$ to 1.2 $\lambda_0$; for example, for a filter of $\lambda_0=620$ nm, the out-of-passband rejection occurs only between 500 and 740 nm. However, for the multifluorescence application, fluorochromes are observed whose spectra extend from 350 to 800 nm. Accordingly, filters were used whose out-of-passband rejection is ensured for ultraviolet at 1200 nm.

Finally, the present invention relates to a labeling kit characterized in that it comprises at least DNA probes as described above or a set of probes as mentioned above.

The present invention relates to a multicolor FISH diagnostic kit, characterized in that it comprises the DNA probes as described above or a set of DNA probes as mentioned above and a combination of filters and of fluorophores as described above.

The FISH or multi-FISH technique to which reference is or will be made several times in the present description is in particular described in Speicher et al., 1996; Schröck et al., 1996.

Other characteristics and advantages of the present invention will emerge on reading the examples below.

The combinations of fluorophores and of optical filters described in the invention may be used in multiple techniques involving fluorescence microscopy. Indeed, the fluorophores described in the present invention may be used to label many molecules or structures. Nonexhaustively, said fluorophores may be used to label polypeptides, antibodies, nucleic acids, phospholipids, fatty acids, sterol derivatives, membranes, organelles and many other biological macromolecules. The organelles may be mitochondria, endoplasmic reticulum, Golgi apparatus and lysosomes.

The combination of fluorophores and of optical filters according to the invention may be used to carry out FISH. In particular, this may allow the simultaneous use of several probes. This combination may be used to study multiple aspects such as cell morphology, the cytoskeleton, cell receptors, ion channels, neurotransmitters, the circulation of fluids, membrane fluidity, cell viability and proliferation, apoptosis, pinocytosis, endocytosis and exocytosis, transduction, pH and ion concentrations (for example calcium, potassium, magnesium and zinc concentrations) (Richard P Haugland, 1996, Molecular Probes, MTZ Spend Ed.). It may allow the study of expression and translation.

The invention therefore also relates to a combination of fluorophores chosen from: fluorescein isothiocyanate (FITC), Texas Red (TR for Texas Red), cyanine 3 (Cy3), cyanine 5 (Cy5), cyanine 5.5 (Cy5.5), cyanine 7 (Cy7), Bodipy 630/650.

Preferably, the combination of fluorophores comprises at least 2, 3, 4, 5, 6 or 7 fluorophores chosen from: fluorescein isothiocyanate (FITC), Texas Red (TR for Texas Red), cyanine 3 (Cy3), cyanine 5 (Cy5), cyanine 5.5 (Cy5.5), cyanine 7 (Cy7), Bodipy 630/650.

A combination of preferred fluorophores of the present invention comprises the following 5 fluorophores: fluorescein isothiocyanate (FITC), Texas Red (TR), cyanine 3 (Cy3), cyanine 5 (Cy5) and cyanine 7 (Cy7).

Another preferred combination of fluorophores of the present invention comprises the following 6 fluorophores: fluorescein isothiocyanate (FITC), Texas Red (TR), cyanine 3 (Cy3), Bodipy 630/650, cyanine 5 (Cy5) and cyanine 7 (Cy7).

Another preferred combination of fluorophores of the present invention comprises the following 6 fluorophores: fluorescein isothiocyanate (FITC), Texas Red (TR), cyanine 3 (Cy3), Bodipy 630/650 and cyanine 5 (Cy5).

The combinations of fluorophores according to the invention may be included in a multicolor FISH diagnostic kit.

The combinations of fluorophores according to the invention may be used to label an entity chosen from polypeptides, antibodies, nucleic acids, phospholipids, fatty acids, sterol derivatives, membranes, organelles and biological macromolecules.

In addition, the invention relates to a combination of fluorophores combined with a pair of optical filters chosen from:

a. the fluorophore FITC having a maximum absorption wavelength of 494 nm and a maximum emission wavelength of 517 nm combined with an excitation filter of the 490DF30 type (Omega Optical) and with an emission filter of the 530DF30 type (Omega Optical), b. the fluorophore Cy3 having a maximum absorption wavelength of 554 nm and a maximum emission wavelength of 568 nm combined with an excitation filter of the 546DF10 type (Omega Optical) and with an emission filter of the 570DF10 type (Omega Optical), c. the fluorophore TR having a maximum absorption wavelength of 593 nm and a maximum emission wavelength of 613 nm combined with an excitation filter of the 590DF10 type (Omega Optical) and with an emission filter of the 615DF10 type (Omega Optical), d. the fluorophore Cy5 having a maximum absorption wavelength of 652 nm and a maximum emission wavelength of 670 nm combined with an excitation filter of the 650DF20 type (Omega Optical) and with an emission filter of the 670DF10 type (Omega Optical), e. the fluorophore Cy7 having a maximum absorption wavelength of 743 nm and a maximum emission wavelength of 767 nm combined with an excitation filter of the 740DF25 type (Omega Optical) and with an emission filter of the 780EFLP type (Omega Optical), f. the fluorophore Cy5.5 having a maximum absorption wavelength of 675 nm and a maximum emission wavelength of 694 nm combined with an excitation filter of the 680DF20 type (Omega Optical) and with an emission filter of the 700EFLP type (Omega Optical), g. the fluorophore Bodipy 630/650 having a maximum absorption wavelength of 632 nm and a maximum emission wavelength of 658 nm combined with an excitation filter of the 630DF20 type (Omega Optical) and with an emission filter of the 650DF10 type (Omega Optical).

Preferably, the combination of fluorophores combined with a pair of optical filters comprises at least 1, 2, 3, 4, 5, 6 or 7 fluorophores and filters chosen from:

a) the fluorophore FITC having a maximum absorption wavelength of 494 nm and a maximum emission wavelength of 517 nm combined with an excitation filter of the 490DF30 type (Omega Optical) and with an emission filter of the 530DF30 type (Omega Optical), b) the fluorophore Cy3 having a maximum absorption wavelength of 554 nm and a maximum emission wavelength of 568 nm combined with an excitation filter of the 546DF10 type (Omega Optical) and with an emission filter of the 570DF10 type (Omega Optical), c) the fluorophore TR having a maximum absorption wavelength of 593 nm and a maximum emission wavelength of 613 nm combined with an excitation filter of the 590DF10 type (Omega Optical) and with an emission filter of the 615DF10 type (Omega Optical), d) the fluorophore Cy5 having a maximum absorption wavelength of 652 nm and a maximum emission wavelength of 670 nm combined with an excitation filter of the 650DF20 type (Omega Optical) and with an emission filter of the 670DF10 type (Omega Optical), e) the fluorophore Cy7 having a maximum absorption wavelength of 743 nm and a maximum emission wavelength of 767 nm combined with an excitation filter of the 740DF25 type (Omega Optical) and with an emission filter of the 780EFLP type (Omega Optical), f) the fluorophore Cy5.5 having a maximum absorption wavelength of 675 nm and a maximum emission wavelength of 694 nm combined with an excitation filter of the 680DF20 type (Omega Optical) and with an emission filter of the 700EFLP type (Omega Optical), g) the fluorophore Bodipy 630/650 having a maximum absorption wavelength of 632 nm and a maximum emission wavelength of 658 mm combined with an excitation filter of the 630DF20 type (Omega Optical) and with an emission filter of the 650DF10 type (Omega Optical).

The combinations of fluorophores combined with the pair of optical filters according to the invention may be included in a multicolor FISH diagnostic kit.

The combinations of fluorophores combined with a pair of optical filters according to the invention may be used to label an entity chosen from polypeptides, antibodies, nucleic acids, phospholipids, fatty acids, sterol derivatives, membranes, organelles and biological macromolecules.

The probes and combinations of fluorophores according to the invention may be used with any type of microscope (monochromator, laser, fluorescence microscope). Preferably, the invention uses a fluorescence microscope.

Various publications and patents are cited in the description. The disclosures contained in the publications and patents identified by references in this application are incorporated by way of reference into the present application for a more detailed description of the content of the present invention.

EXAMPLES

Example 1

Preparation of the Probes

The genomic DNA extracted from various human-rodent somatic hybrid lines (NIGMS Human genetic Mutant Cell Repository, Coriell Institute for Medical Research, Camdem) (Table 1) served as template for the PCR.

TABLE 1

| Chromosome | Line reference |
| --- | --- |
| 1 | GM 13139 |
| 2 | GM 10826B |
| 3 | GM 10253 |
| 4 | GM 10115 |
| 5 | GM 10114 |
| 6 | GM 11580 |
| 7 | GM 10791 |
| 8 | GM 10156C |
| 9 | GM 10611 |
| 10 | GM 10926B |
| 11 | GM 10927A |
| 12 | GM 10868 |
| 13 | GM 10898 |
| 14 | GM 11535 |
| 15 | GM 11715 |
| 16 | GM 10567 |
| 17 | GM 10498 |
| 18 | GM 11010 |
| 19 | GM 10449 |
| 20 | GM 13260 |
| 21 | GM 10323 |
| 22 | GM 10888 |
| X | GM 6318B |

The PCR was carried out either in the presence solely of the primer SR1 (situated at the 3' end of the Alu consensus sequence, position 241 to 261: 5' CCACTGCACTCCAGC-CTGGG 3' (SEQ ID No. 1) (Romana et al., 1993), or in the presence of the primer SR1 and of the primer L1H:

5' CATGGCACATGTATACATATGTAAC(A/T)AACC 3' (SEQ ID No. 2 and No. 3) (Ledbetter et al., 1990). When only the primer SR1 was used in the PCR, the product of amplification labeled and used as probe on metaphase chromosomes was stained almost completely the corresponding chromosome [sic] (with the exception of the centromeric regions) with an R-type band profile (as has been described by Lichter et al., 1990 with other types of Alu primers). However, in order to have a representation of the negative R bands, a PCR was also carried out by incorporating the 2 primers: SR1 and L1. Thus, when the 2 products of amplification (SR1 and SR1/L1) were mixed and used as probe, the negative R bands were indeed stained and the telomeric regions were perfectly delimited.

PCR Conditions

The PCR reaction took place in a final volume of 50 μl containing 500 ng of genomic DNA (somatic hybrid), 1 μM of each oligonucleotide (either 1 μM SR1, or 1 μM SR1 and 1 μM L1H), 10 mM Tris-HCl, 50 mM KCl, 2.5 mM MgCl$_2$, 0.01% gelatin, 250 μM of each deoxynucleotide triphosphate (dATP, dGTP, dCTP, dTTP) and 2.5 U of *Thermophilus aquaticus* DNA polymerase (Perkin-Elmer-Cetus). The initial denaturation was carried out at 96° C. for 6 min, followed by 30 cycles: denaturation at 94° C. for 1 min, annealing at 63° C. for 1 min, extension at 72° C. for 10 min. At the end of the cycles, a final extension at 72° C. for 10 min was carried out.

The 2 products of amplification (SR1 and SR1/L1H) were mixed and then precipitated with ethanol. The DNA pellet was taken up in 20 μl of water and the DNA concentration was estimated on a 1.3% agarose gel.

Labeling of the Probes by "Nick Translation"

15 μg of the mixture of PCR products were able to be labeled during a single Nick translation reaction. The reaction took place in a final volume of 500 μl, containing 20 μM of each of the deoxynucleotide triphosphates (dATP, dGTP, dCTP), 10 μM of dTTP and 10 μM of modified dUTP, 50 μM Tris-HCl, 5 μM MgCl$_2$, 1 μM β-mercaptoethanol and 20 U of a mixture of enzymes (Dnase/Polymerase:Boehringer-Mannheim). To directly label the probe in fluorescence, the modified nucleotide was either dUTP-12-FITC (Boehringer-Mannheim) or dUTP-12-Texas Red (Molecular Probes) or dUTP-Cy3 (Amersham) or dUTP-Cy5 (Amersham). On the other hand, for an indirect labeling, dUTP-16-biotinylated (Boehringer-Mannheim) was used. The labeling was carried out in an Eppendorf tube (2 ml) overnight at 15–16° C. The free nucleotides were then removed by precipitation of the probe with ethanol. The DNA pellet was taken up in 500 μl of TE 10:1 (10 mM Tris-HCl, 1 mM EDTA, pH 8) so that the probe is at a concentration of about 30 ng/μl.

Composition of the Mixture of the 23 Chromosome Paint Probes

Each probe specific for a chromosome was labeled individually with the various modified dUTPs (fluorescent or otherwise). Depending on the richness in R and G bands of each of the chromosomes and depending on their size, those which had or otherwise to be composed of different fluorochromes were established a priori. For example, combinations of 3 or 4 fluorochromes were preferably used for chromosomes rich in R bands (e.g.: chromosome 19); on the other hand, for chromosomes low in R bands, only 1 to 2 fluorochromes were used (e.g.: chromosome 8). This choice also depended, for each fluorochrome, on the combination of excitation and emission filters. Indeed, when a probe was labeled in equivalent proportion with different fluorochromes, the signal intensities for the different fluorochromes are not necessarily comparable. That depends indeed on the quality of the excitation and emission filters for each fluorochrome, but also on the quantity of fluorescence emitted by the fluorochrome. The latter itself depends on the intensity of the excitation luminous flux and therefore on the spectral power of the light source (Mercury Lamp HBO 100 W-OSRAM). Among all these parameters, it was preferably chosen to optimize the resolving power of the combinations of filters, in order to obtain on emission the best signal/background noise ratio for each fluorochrome. Indeed, the differences in intensity of fluorescence may be compensated for, on the one hand, by increasing or decreasing the exposure time during the acquisition of the image by the camera (Hamamatsu C4880), but also by varying the concentrations of probes depending on the fluorescent marker used. Finally, the concentrations of probes were adjusted such that for a given fluorochrome (and therefore for a given filter combination), all the labeled chromosomes emit a fluorescence of equivalent intensity.

The composition of the 23 chromosome paint probes was therefore defined experimentally and precisely after many control experiments (Table 2).

400 μg (about 27-fold) of Cot1 DNA (human competitor DNA) were added to these 1470 ng of mixture of chromosomal probes (50 different probes). The DNA mixture was then precipitated with ethanol. The pellet was taken up in 10 μl of hybridization mixture (50% formamide, 10% dextran sulfate, 2×SSC (pH 7), 1 μg/μl of sonicated herring sperm DNA).

TABLE 2

| Fluor Chrom. | FITC | Cy3 | TR | Cy5 | Bio/Cy7 | Mixture 1470 ng = |
|---|---|---|---|---|---|---|
| 1 |  | 35 |  |  |  | 35 |
| 2 |  |  | 40 |  |  | 40 |
| 3 | 30 |  |  | 25 |  | 55 |
| 4 |  |  | 50 |  |  | 50 |
| 5 | 50 |  |  |  |  | 50 |
| 6 |  |  |  | 40 | 30 | 70 |
| 7 |  | 30 |  |  | 35 | 65 |
| 8 | 60 |  |  | 30 |  | 90 |
| 9 | 30 | 20 |  |  |  | 50 |
| 10 |  | 30 | 25 |  | 20 | 75 |
| 11 |  | 30 |  | 40 |  | 70 |
| 12 |  |  | 35 | 50 |  | 85 |
| 13 | 60 |  | 45 |  |  | 105 |
| 14 | 25 | 20 |  |  | 25 | 70 |
| 15 | 50 | 15 | 15 |  |  | 80 |
| 16 | 30 | 20 |  | 20 |  | 70 |
| 17 |  | 15 |  | 25 | 20 | 60 |
| 18 |  |  |  |  | 40 | 40 |
| 19 | 25 | 10 | 20 |  | 20 | 75 |
| 20 |  | 20 | 20 | 30 |  | 70 |
| 21 |  | 30 | 30 |  |  | 60 |
| 22 | 10 |  |  | 15 | 20 | 45 |
| X |  | 30 |  |  | 30 | 60 |

Full name of the fluorochromes:
FITC: Fluorescein isothiocyanate; TR: Texas Red; Cy3: Cyanine 3; Cy5: Cyanine 5; Bio: Biotin; Cy7: Cyanine 7

An Alternative Preparation of the Probes

Alternatively, the preparation of the mixture of probes was carried out before their labeling by Nick translation for each fluorochrome (Table 3). 5 mixtures of probes were thus obtained which were labeled by Nick translation with the aid of modified nucleotides according to the following protocol.

1 to 2 μg of the mixture of probes were labeled by Nick translation in a volume of 50 μl containing: 20 μM of each of the deoxynucleotide triphosphates (dATP, dGTP, dCTP), 10 μM of dTTP and 10 μM of modified dUTP, 50 μM Tris-HCl, 5 μM MgCl$_2$, 1 μM β-mercaptoethano and 20 U of a mixture of enzymes (Dnase/Polymerase:Boehringer-Mannheim). To directly label the probe in fluorescence, the modified nucleotide was dUTP-12-FITC (Boehringer-Mannheim) or dUTP-12-Texas Red (Molecular Probes) or dUTP-Cy3 (Amersham) or dUTP-Cy5 (Amersham). On the other hand, for an indirect labeling, dUTP-16-biotinylated (Boehringer-Mannheim) was used. The labeling was carried out in an Eppendorf tube (2 ml) overnight at 15–16° C.

After labeling, the 5 mixtures of chromosomal probes (14.75 μg) were precipitated together (with ethanol) in the presence of 400 μg (about 27-fold) of Cot1 DNA (human competitor DNA). The pellet was taken up in 10 μl of hybridization mixture (50% formamide, 10% dextran sulfate, 2×SSC (pH 7), 1 μg/μl of sonicated herring sperm DNA).

This alternative method of labeling has the advantage of making the protocol for labeling the probes less cumbersome and simpler by reducing the number of labelings by Nick translation to five instead of fifty and by preparing a single mixture of probes instead of two.

Example 2

Fluorescence in situ Hybridization

The procedure was that described by Cherif et al., 1990, with a few modifications.

Preparation of the Chromosomes in Metaphase

The preparation of the metaphase chromosomes was carried out starting with a culture of circulating lymphocytes obtained by venous puncture of a normal subject. The lymphocytes stimulated by phytohemagglutinin (PHA) (100 μl per 8 ml of culture) were cultured for 72 hours at 37° C. in RPMI-1640 medium. The cells were then synchronized by adding methotrexate (10 μM) for 17 hours and then rinsed and recultured in the presence of 5-bromdeoxyuridine (BrdU) (0.1 mM) for 6 hours. After the action of colchicine (1 mg/ml) for 15 min, the disruption of the cells was obtained by resuspension in a hypotonic KCl solution (75 mM). The chromosomes were fixed in a methanol/acetic acid mixture (3 vol/1 vol) and one to two drops of cellular suspension were spread on each slide. The slides, dried at room temperature for 2 to 3 days, were then stored at −20° C. for several months.

TABLE 3

| Fluor Chrom. | FITC | Cy3 | TR | Cy5 | Bio/Cy7 | Mixture |
|---|---|---|---|---|---|---|
| 1 |  | 0.3 |  |  |  | 0.3 |
| 2 |  |  | 0.4 |  |  | 0.4 |
| 3 | 0.3 |  |  |  | 0.25 | 0.55 |
| 4 |  |  |  | 0.5 |  | 0.5 |
| 5 | 0.5 |  |  |  |  | 0.5 |
| 6 |  |  |  | 0.4 | 0.3 | 0.7 |
| 7 |  |  | 0.3 |  | 0.35 | 0.65 |
| 8 | 0.6 |  |  | 0.3 |  | 0.9 |
| 9 | 0.3 | 0.2 |  |  |  | 0.5 |
| 10 |  | 0.3 | 0.25 |  | 0.2 | 0.75 |
| 11 |  | 0.3 |  | 0.4 |  | 0.7 |
| 12 |  |  | 0.35 | 0.5 |  | 0.85 |
| 13 | 0.6 |  | 0.45 |  |  | 0.105 |
| 14 | 0.25 | 0.2 |  |  | 0.25 | 0.7 |
| 15 | 0.5 | 0.15 | 0.15 |  |  | 0.8 |
| 16 | 0.3 | 0.2 |  | 0.2 |  | 0.7 |
| 17 |  | 0.15 |  | 0.25 | 0.2 | 0.6 |
| 18 |  |  |  |  | 0.4 | 0.4 |
| 19 | 0.25 | 0.1 | 0.2 |  | 0.2 | 0.75 |
| 20 |  | 0.2 | 0.2 | 0.3 |  | 0.7 |
| 21 |  | 0.3 | 0.3 |  |  | 0.6 |
| 22 | 0.1 |  |  | 0.15 | 0.2 | 0.45 |
| X |  | 0.3 |  |  | 0.3 | 0.6 |
| Total (μg) | 3.7 | 2.7 | 2.75 | 3.15 | 2.45 | 14.75 |

Full name of the fluorochromes:
FITC: Fluorescein isothiocyanate; TR: Texas Red; Cy3: Cyanine 3; Cy5: Cyanine 5; Bio: Biotin; Cy7: Cyanine 7

Preparation of the Slides

The slides were treated with RNase (100 μg/ml) for 1 hour at 37° C. and then rinsed 3 times (5 min each) in a 2×SSC solution, pH 7. The slides were then dehydrated by successive passes in a series of ethanol baths at increasing concentration (70%, 80%, 90% and 100% and 2 min per bath), and dried. The chromosomal DNA was denatured by immersing the slides in a 70% formamide/2×SSC bath (pH 7) at 70° C. for 2 minutes. The denaturation was stopped by immersing the slides (2 minutes) in 70% ethanol cooled to −20° C. and kept in an ice bath. The slides were then dehydrated by successive passes in a series of ethanol baths at increasing concentration and dried. The slides were then incubated for 8 to 10 min at 37° C. in a solution (20 mM Tris-HCl, pH 7.4, 2 mM $CaCl_2$) containing proteinase K (100 ng/ml) and then dehydrated in a series of ethanol baths and dried.

Hybridization and Detection of the Signal

The mixture of probes and of competitor DNA (10 µl) was denatured for 10 min at 70° C. and then immersed in ice and prehybridized for at least 3 hours at 37° C. This mixture was then deposited on the slide and covered with a glass coverslip (18×22 mm). The hybridization took place over 2–3 days at 37° C. in a humid chamber.

The slides were then washed in a series of 3 baths of 50% formamide, 2×SSC, pH 7 (3 min each) at a temperature of 42–45° C., followed by 5 washes in 2×SSC, pH 7 (2 minutes each) and by a one minute wash in a 1×BN solution (0.1 M sodium bicarbonate, 0.05% nonidet P-40). The biotinylated probes were detected by adding avidin (Vector Laboratories Biosys) coupled to cyanine 7 (Amersham) (Avidin-Cy7) (5 µg/ml). The coupling of the avidin to cyanine 7 was carried out with a coupling kit (Amersham). To reduce the problems of background noise linked to nonspecific bindings of avidin, the slides were previously incubated for 10 minutes in a 1×BN solution containing 5% skimmed milk powder. The slides were then incubated for ½ an hour at 37° C. in a solution containing avidin-Cy7 (5 µg/ml in 1×BN+5% milk powder) and then successively washed 3 times (2 minutes) in a 1×BN solution at 45° C. The fluorescent signal was amplified by adding a layer of biotinylated anti-avidin antibodies (5 µg/ml) (Vector Laboratories, Biosys France), followed by a layer of avidin-Cy7 (5 µg/ml) according to the protocol described by Pinkel et al., 1986. For each layer, the slides were incubated for 30 minutes at 37° C. and then washed 3 times in a 1×BN solution. The probes labeled with dUTP-FITC, dUTP-TR, dUTP-Cy3 and dUTP-Cy5 required no additional revealing step.

The slides were examined with the aid of an epifluorescence photomicroscope (DMRX B, LEICA) equipped with the combination of filters which is described above. Two independent wheels were used to carry 8 filters each. The wheel carrying the excitation filters was inserted immediately after the Hg lamp and that carrying the emission filters was placed above the objectives and the beam separating filter. Before the acquisition of the images, 20 µl of an anti-fade solution (Johnson et al., 1981) were deposited on each slide and covered with a coverslip (anti-fade solution: 100 mg of PPD (p-phenylenediamine, Sigma) in a solution composed of 10 ml of PBS and 90 ml of glycerol; the pH of the solution was adjusted to 8.0 with 0.1 M NaOH). The anti-fade solution makes it possible to avoid the rapid extinction of the fluorescence emitted by the different fluorochromes when they are subjected to strong irradiation.

Example 3

Example of Use of a Combination of 6 Fluorophores

Since cyanine 7 is a relatively unstable fluorochrome, efforts were made to replace it with another fluorochrome, for example Bodipy 630/650 (Molecular Probes). Coupled to an antibody or a molecule of avidin, Bodipy makes it possible to indirectly reveal a probe labeled with biotin, with digoxigenin or with dinitrophenol (DNP). In this case, the choice of the 5 fluorochromes for the multifluorescence can no longer be the same because the absorption and emission spectra of cyanine 5 and of Bodipy 630/650 are too close for there to be good discrimination between these two fluorochromes. The choice will be the following:

fluorescein isothiocyanate (FITC)

Texas Red (TR)

Cyanine 3 (Cy3)

Bodipy 630/650

Cyanine 5.5 (Cy5.5)

This choice also has the advantage of allowing the use of cyanine 7 as 6th fluorochrome if need be (for example for applications where it is not possible to carry out combinatory probe labeling, and where it would be advantageous to have different probes which can be discriminated between with a maximum of different fluorochromes).

In this case, the Cy5.5 should also be coupled to an antibody or a molecule of avidin in order to be able to reveal a probe labeled with biotin, digoxigenin or DNP.

For example, for multifluorescence karyotyping, the different systems for labeling and revealing the probes will be:

| Labeling | Type of labeling | Revealing |
|---|---|---|
| fluorescein isothiocyanate (FITC) | direct | no |
| Texas Red (TR) | direct | no |
| Cyanine 3 (Cy3) | direct | no |
| digoxigenin (Dig) | indirect | anti-dig-Bodipy 630/650 |
| biotin (Bio) | indirect | avidin-Cy5.5 |

Should it be desirable to use 6 fluorochromes at the same time, the choice would be:

| Labeling | Type of labeling | Revealing |
|---|---|---|
| fluorescein isothiocyanate (FITC) | direct | no |
| Texas Red (TR) | direct | no |
| Cyanine 3 (Cy3) | direct | no |
| dinitrophenol (DNP) | indirect | anti-DNP Bodipy 630/650 |
| digoxigenin (Dig) | indirect | anti-dig-Cy5.5 |
| biotin (Bio) | indirect | avidin-Cy7 |

Although the preferred embodiments of the invention have been illustrated and described, it should be considered that many changes may be made by persons skilled in the art to depart from the spirit and scope of the present invention.

REFERENCES

Cherif D., Julier C., Delattre O., Derre J., Lathrop G M., Berger R., (1990). Simultaneous localization of cosmids and chromosome R-banding by fluorescence microscopy: Application to regional mapping of chromosome 11. Proc. Natl. Acad. Sci. USA 87, 6639.

Dutrillaux B., Lejeune J. (1971). Sur une nouvelle technique d'analyse du caryotype humain (On a new technique for analyzing human karyotype). C.R. Acad. Sci. 272, 2638.

Johnson G. D., De Nogueira C., Aranjo J. G. M. (1981). A simple method for reducing the fading of immunofluorescence during microscopy. J. Immunol. Methods 43, 349.

Korenberg J. R., Rikowski M. C. (1988). Human genome organization: Alu, Lines and the molecular structure of metaphase chromosome bands. Cell 53, 391.

Ledbetter S. A., Garcia-Heras J., Ledbetter D. H. (1990). "PCR-karyotype" of human chromosomes in somatic cell hybrids. Genomics 8, 614.

Lichter P., Ledbetter S. A., Ledbetter D. H., Ward D. C. (1990). Fluorescence in situ hybridization with Alu and L1 polymerase chain reaction probes for rapid characterization of human chromosomes in hybrid cell lines. Proc. Natl. Acad. Sci. USA 87, 6634.

Pinkel D., Straume T., Gray J. W. (1996). Cytogenetic analysis using quantitative, high sensitivity fluorescence hybridization. Proc. Natl. Acad. Sci. USA 83, 2934.

Richard P Haugland, 1996, Molecular Probes, MTZ Spence Ed. <<Handbook of fluorescent probes and research chemicals>>

Romana S. P., Tachdjian G., Druart L., Cohen D., Berger R., Cherif D. (1993). A simple method for prenatal diagnosis of trisomy 21 on uncultured amniocytes. Eur. J. Hum. Genet. 1, 245.

Sabile A., Poras I., Cherif D., Goodfellow P., Avner P. (1997). Isolation of monochromosomal hybrid for mouse chromosomes 3, 6, 10, 12, 14 and 18. Mammalian Genome 8, 81.

Schröck E., du Manoir S., Veldman T., Schoell B., Wienberg J., Ferguson-Smith M. A., Ning Y., Ledbetter D. H., Bar-Am I., Soenksen D., Garini Y., Ried T. (1996). Multicolor spectral karyotyping of human chromosomes. Science 273, 494–497.

Speicher M. R., Ballard S. G., Ward D C. (1996). Karyotyping human chromosomes by combinatorial multi-fluor FISH. Nature Genetics 12, 368–375.

Summer A. T., Evans H. J., Buckland R. A. (1971). A new technique for distinguishing between human chromosomes. Nature (New Biol) 232, 31.

What is claimed is:

1. A method of identifying human chromosomes comprising performing a multicolor FISH analysis using a set of nucleic acid probes for labeling one or more human chromosomes and hybridizing said one or more human chromosomes with said set of nucleic acid probes, said set of nucleic acid probes comprising a mixture of two interspersed repeated sequence-polymerase chain reaction (IRS-PCR) amplification products from said chromosome(s), wherein:

the first amplification product is complementary to either a specific primer for Alu DNA sequences or a specific primer for long interspersed element (LINE) sequences;

the second amplification product is complementary to a specific primer for Alu DNA sequences and a specific primer for LINE DNA sequences; and each of said probes, being specific for one or more human chromosomes, are directly or indirectly labeled with:

a) a fluorophore having an absorption bandwidth wavelength interval spanning 593 nm and an emission bandwidth wavelength interval spanning 613 nm; and b) a fluorophore having an absorption bandwidth wavelength interval spanning 554 nm and an emission bandwidth wavelength interval spanning 568 nm; and c) up to five (5) fluorophores selected from the group consisting of:

i) a fluorophore having an absorption bandwidth wavelength interval spanning 494 nm and an emission bandwidth wavelength interval spanning 517 nm;

ii) a fluorophore having an absorption bandwidth wavelength interval spanning 652 nm and an emission bandwidth wavelength interval spanning 670 nm;

iii) a fluorophore having an absorption bandwidth wavelength interval spanning 675 nm and an emission bandwidth wavelength interval spanning 694 nm;

iv) a fluorophore having an absorption bandwidth wavelength interval spanning 743 nm and an emission bandwidth wavelength interval spanning 767 nm;

v) and a fluorophore having an absorption bandwidth wavelength interval spanning 632 nm and an emission bandwidth wavelength interval spanning 658 nm; and identifying said one or more labeled human chromosomes by fluorescence microscopy, wherein the overlapping of the absorption and emission bandwidth wavelength intervals between the different fluorophores is minimal and there is no overlapping between the absorption and emission maximum of the different fluorophores; and wherein each of said fluorophores having a specific absorption and emission wavelength is combined with a pair of optical filters, one for absorption and one for emission in a fluorescent microscope.

2. The method according to claim 1, wherein said set of nucleic acid probes comprises at least one probe for each of the human chromosomes or for a number of them.

3. The method according to claim 1, wherein said amplification products comprise amplification products obtained from one or more mono-chromosomal rodent-human somatic hybrid.

4. The method according to claim 1, wherein said first amplification product comprises an amplification product obtained using said primer specific for the Alu DNA sequences.

5. The method according to claim 1, wherein said first amplification product comprises an amplification product obtained using said specific primer for LINE DNA sequences.

6. The method according to claim 1, wherein said amplification products comprise amplification products more represented in one type of cytogenetic bands.

7. The method according to claim 6, wherein said amplification products are more represented in the R bands.

8. The method according to claim 1, wherein said specific primers comprise a sequence selected from the group consisting of:

SEQ ID No. 1 for the primer specific for the Alu DNA sequences; and

SEQ ID Nos. 2 and 3 for the primer specific for the LINE DNA sequences.

9. The method according to claim 1, wherein said multicolor FISH analysis is a karyotype analysis.

* * * * *

UNITED STATES PATENT AND TRADEMARK OFFICE
CERTIFICATE OF CORRECTION

PATENT NO.    : 6,905,828 B2
DATED         : June 14, 2005
INVENTOR(S)   : Dorra Cherif It is certified that error appears in the above-identified patent and that said Letters Patent is hereby corrected as shown below:

Column 8,
Line 6, "T ≧ 50%" should read -- T ≥ 50% --.
Line 8, "≦ 7 mm" should read -- ≤ 7 mm --.

Column 10,
Line 64, "658 mm" should read -- 658 nm --.

Column 13,
Line 45, "Blo;" should read -- Bio; --.

Signed and Sealed this

Twenty-seventh Day of September, 2005

JON W. DUDAS
*Director of the United States Patent and Trademark Office*

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<221> NAME/KEY: primer_bind
<222> LOCATION: 1..20
<223> OTHER INFORMATION: primer PCR Alu

<400> SEQUENCE: 1
ccactgcact ccagcctggg                    20

<210> SEQ ID NO 2
<211> LENGTH: 30
<212> TYPE: DNA
<213> ORGANISM: Artificial Sequence
<220> FEATURE:
<221> NAME/KEY: primer_bind
<222> LOCATION: 1..30
<223> OTHER INFORMATION: primer PCR LINE

<400> SEQUENCE: 2
catggcacat gtatacatat gtaacaaacc          30

<210> SEQ ID NO 3
<211> LENGTH: 30
<212> TYPE: DNA
<213> ORGANISM: Artificial Sequence
<220> FEATURE:
<221> NAME/KEY: primer_bind
<222> LOCATION: 1..30
<223> OTHER INFORMATION: primer PCR LINE

<400> SEQUENCE: 3
catggcacat gtatacatat gtaactaacc          30